(12) United States Patent
Uchida et al.

(10) Patent No.: US 7,176,305 B2
(45) Date of Patent: Feb. 13, 2007

(54) PRODUCTION METHOD FOR PURINE NUCLEOTIDE DERIVATIVE DISODIUM CRYSTALS AND ALCOHOL REMOVING METHOD

(75) Inventors: Hiroshi Uchida, Kawasaki (JP); Toyokazu Kaneko, Kawasaki (JP); Tsuyoshi Fujiwara, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 477 days.

(21) Appl. No.: 10/703,506

(22) Filed: Nov. 10, 2003

(65) Prior Publication Data

US 2004/0101897 A1    May 27, 2004

(30) Foreign Application Priority Data

Nov. 22, 2002    (JP)    ............................. 2002-340008

(51) Int. Cl.
*C07H 19/00* (2006.01)
*C12Q 1/68* (2006.01)

(52) U.S. Cl. ...................... 536/26.1; 536/26.71; 435/6
(58) Field of Classification Search ............ 536/26.71; 435/6
See application file for complete search history.

(56) References Cited

U.S. PATENT DOCUMENTS

2002/0177702 A1    11/2002    Tachibana et al.

FOREIGN PATENT DOCUMENTS

| JP | 45-17578 | * | 6/1970 |
| JP | 2001-334102 | | 12/2001 |
| JP | 2002-284794 | | 10/2002 |
| KR | 2002-0092166 | | 12/2002 |

OTHER PUBLICATIONS

Derwent Publications, AN 1990-258697, XP-002276603, KR 8 903 253, Aug. 31, 1989.

* cited by examiner

*Primary Examiner*—Shaojia Anna Jiang
*Assistant Examiner*—Ganapathy Krishnan
(74) *Attorney, Agent, or Firm*—Oblon, Spivak, McClelland, Maier & Neustadt, P.C.

(57) ABSTRACT

Purine nucleotide derivative disodium crystals having a minimized amount of remaining alcohol such as methanol, ethanol or a mixture thereof are produced by overdrying purine nucleotide derivative disodium crystals containing the alcohol; and bringing the overdried purine nucleotide derivative disodium crystals into contact with an aqueous solution containing a hydrophilic organic solvent to control the humidity of the purine nucleotide derivative disodium crystals under a high humidity condition.

17 Claims, No Drawings

PRODUCTION METHOD FOR PURINE NUCLEOTIDE DERIVATIVE DISODIUM CRYSTALS AND ALCOHOL REMOVING METHOD

CROSS REFERENCES TO RELATED APPLICATIONS

This application claims priority to Japanese Patent Application No. 2002-340008, filed on Nov. 22, 2002.

BACKGROUND OF THE INVENTION

1) Field of the Invention

The present invention relates to a method for producing crystals of purine nucleotide derivative disodium, which are important as flavorings and pharmaceutical products. More particularly, the present invention relates to a method for removing an alcohol such as methanol, from purine nucleotide derivative disodium crystals that efficiently removes the alcohol, from crystals containing methanol, for example, those crystals obtained by crystallization from methanol (hereinafter, also "methanol crystallization"). Furthermore, the present invention relates to a method for producing purine nucleotide derivative disodium crystals that involves the use of the method for removing methanol (hereinafter, also "methanol removing method").

2) Description of the Related Art

Crystals of purine nucleotide derivative disodium such as crystals of 5'-guanylic acid disodium (hereinafter, "5'-GMP2Na") are important for producing flavorings and pharmaceutical products. The purine nucleotide derivative disodium crystals are obtained by crystallization in the copresence of methanol. However, methanol in the crystals in unacceptable amounts unless any other treatment is performed. When the purine nucleotide derivative disodium crystals are used for application to food or pharmaceutical products, it is necessary to reduce the content of methanol to a predetermined upper limit.

Purine nucleotide derivative disodium crystals such as 5'-GMP2Na crystals contain about 23% to about 24% of water as crystal water. Since methanol is present mostly in the crystal water, it is difficult to remove it from the crystals unlike the case where methanol or ethanol is attached to the surface of crystals. For example, when crystals are obtained in a system in which methanol coexists and allowed to stand at ambient temperature (e.g., about 20±15° C.), considerable amounts of methanol remain in the crystals; for example, about 100 parts per million of methanol remains in the crystals even after 24 hours. Similar problems are encountered when crystals of purine derivative nucleotide disodium crystals are formed in ethanol or a mixture of methanol and ethanol.

SUMMARY OF THE INVENTION

It is therefore necessary to perform a treatment that removes the alcohol such as methanol or ethanol that still remains in the crystals. In general, even if the crystals of a purine nucleotide derivative disodium are simply dried, the alcohol such as methanol or ethanol is rarely removed from the crystals. However, the inventors of the present invention (hereinafter, "the inventors") have found that methanol or ethanol can be removed by bringing the crystals into contact with humidity-controlled air or vapor, thereby replacing the alcohol with moisture or water.

The inventors also found that the contents of methanol or ethanol in crystals is further reduced by reducing the water content of the crystals containing residual methanol by drying the crystals and then humidifying the crystals with humidity-controlled air. Based on these findings, the inventors have attempted to produce crystals that are substantially free of alcohols such as methanol and ethanol by excessively drying the crystal water to produce overdried crystals that have a reduced water content, followed by bringing the overdried crystals into contact with vapor or humidified air to remove the remaining alcohol such as methanol or ethanol.

However, this approach tends to cause agglomeration of crystals, and as a result the yield of the crystal product is decreased. Therefore, this approach needs improvement so that it can be useful as a production method on an industrial scale. In addition, although methanol or ethanol is removed in a shorter time by the aforementioned method than the time required by,the method of drying crystals that includes simply allowing the crystals to stand after the methanol crystallization or ethanol crystallization, the time required for removing methanol or ethanol must be as short as possible. This is because the standing the crystals after methanol crystallization or ethanol crystallization as they are is accompanied by risks, for example, contamination by microbes, so that management of the humidity controlling process on the site must be highly accurate. Accordingly, it is desired to further reduce the time required for removing methanol or ethanol. The inventors have further tried to control the humidity of the crystals to remove methanol or ethanol in a shorter time. More specifically, the inventors tried to-control the humidity of crystals by spraying pure water to the crystals after subjecting them to an overdrying treatment. However, this approach resulted in significant agglomeration of the crystals and turned out impractical for industrial production.

It is an object of the present invention to suppress agglomeration of crystals that causes a decrease in the yield, and to remove an alcohol such as methanol or ethanol from the purine nucleotide derivative disodium crystals to reduce the content of methanol or ethanol of the crystals to a predetermined low level, thereby producing the purine nucleotide derivative disodium crystals more efficiently.

The inventors have further conducted intensive studies to develop a method for removing the remaining alcohol such as methanol or ethanol from crystals in a shorter time without generating agglomeration of crystals. As a result, they found that the generation of agglomeration of crystals can be prevented by adding an aqueous solution that contains a water soluble organic solvent directly to the crystals, thereby removing the remaining alcohol to a low level in an extremely short time. Based on this finding, the present invention has been achieved.

The present invention provides:

1) A method of producing purine nucleotide derivative disodium crystals, including: crystallizing a purine derivative nucleotide disodium in a solution of an alcohol composed of one member selected from the group consisting of methanol, ethanol and mixtures thereof to form purine derivative nucleotide disodium crystals; performing solid-liquid separation of the purine nucleotide derivative disodium crystals containing the alcohol; overdrying the separated purine nucleotide derivative disodium crystals; and bringing the overdried purine nucleotide derivative disodium crystals into contact with an aqueous solution containing a hydrophilic organic solvent to control the humidity of the purine nucleotide derivative disodium crystals under a predetermined humidity condition.

2) The method according to 1) above, wherein the overdrying includes drying the purine nucleotide derivative disodium crystals with the controlled humidity to a hydrate equivalent water content of at most 5 hydrates.

3) The method according to 1) above, wherein the hydrophilic organic solvent is at least one solvent selected from the group consisting of methanol, ethanol, and propanol.

4) The method according to 2) above, wherein the hydrophilic organic solvent is at least one solvent selected from the group consisting of methanol, ethanol, and propanol.

5) The method according to 1) above, wherein the humidity condition is a relative humidity of 20% to 90%.

6) The method according to 2) above, wherein the humidity condition is a relative humidity of 20% to 90%.

7) The method according to 3) above, wherein the humidity condition is a relative humidity of 20% to 90%.

8) The method according to 1) above, wherein the purine nucleotide derivative disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

9) The method according to 2) above, wherein the purine nucleotide derivative disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

10) The method according to 3) above, wherein the purine nucleotide derivative disodium crystals comprise at least one member selected from the-group consisting of 5'-guanylic acid disodium crystals, 5'-inosinic acid disodium crystals, and mixed crystals of 5'-guanylic acid disodium and 5'-inosinic acid disodium.

11) The method according to 4) above, wherein the purine nucleotide derivative disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

12) A method of removing an alcohol from purine nucleotide derivative disodium crystals, comprising: overdrying the purine nucleotide derivative disodium crystals containing an alcohol composed of one member selected from the group consisting of methanol, ethanol, and mixtures thereof; and bringing the overdried purine nucleotide derivative disodium crystals into contact with an aqueous solution containing a hydrophilic organic solvent to control the humidity of the purine nucleotide derivative disodium crystals under a predetermined humidity condition.

13) The method according to 12) above, wherein the purine nucleotide derivative disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

14) A method of producing purine nucleotide derivative disodium crystals, comprising: performing solid-liquid separation of the purine nucleotide derivative disodium crystals an alcohol composed of one member selected from the group consisting of methanol, ethanol, and mixtures thereof; overdrying the separated purine nucleotide derivative disodium crystals; and bringing the overdried purine nucleotide derivative disodium crystals into contact with an aqueous solution containing a hydrophilic organic solvent to control the humidity of the purine nucleotide derivative disodium crystals under a predetermined humidity condition.

15) The method according to 14) above, wherein the overdrying includes drying the purine nucleotide derivative disodium crystals with the controlled humidity to a hydrate equivalent water content of at most 5 hydrates.

16) The method according to 14) above, wherein the hydrophilic organic solvent is at least one solvent selected from the group consisting of methanol, ethanol, and propanol.

17) The method according to 14) above, wherein the humidity condition is a relative humidity of 20% to 90%.

18) The method according to 14) above, wherein the purine nucleotide derivative disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

According to the present invention, there is provided a method of efficiently producing purine nucleotide derivative disodium crystals whose alcohol content has been decreased to a predetermined acceptable level in high yields while preventing agglomeration of crystals. Furthermore, according to the present invention, alcohols such as methanol and ethanol can be efficiently removed from purine nucleotide derivative disodium crystals containing such an alcohol to a predetermined low level while preventing agglomeration of crystals.

The other objects, features and advantages of the present invention are specifically set forth in or will become apparent from the following detailed descriptions of the invention.

DETAILED DESCRIPTION

The method of producing purine nucleotide derivative disodium crystals according to the present invention (hereinafter, "the production method of the present invention") is efficient for removing an alcohol such as methanol, ethanol, or a mixture thereof that remains in the crystals while suppressing agglomeration of crystals. The term "purine nucleotide derivative" as used herein refers to a nucleotide derivative having a purine as a base. The term "purine" means a base having a purine skeleton and includes, for example, adenine, guanine, hypoxanthine, and xanthine. Specific examples of the purine nucleotide derivative include adenylic acid (hereinafter, "AMP"), guanylic acid (hereinafter, "GMP"), inosinic acid (hereinafter, "IMP"), and xanthosinic acid (hereinafter, "XMP"). The present invention can be particularly preferably applied to production of 5'-GMP2Na crystals, 5'-inosinic acid disodium crystals (hereinafter, "5'-IMP2Na crystal"), and mixed crystals of 5'-guanylic acid disodium and 5'-inosinic acid disodium (hereinafter, "I+G mixed crystal"). The term "mixed crystals" as used herein refers to crystals composed of a mixture of two or more kinds and exhibiting a uniform crystalline phase.

In one embodiment, the production method of the present invention includes a crystallization step, a solid/liquid separation step, an overdrying step, and a humidity control step. In the crystallization step, so-called alcohol crystallization, typically methanol crystallization or ethanol crystallization is performed. The crystallization process is not limited to these and, for example, the process of crystallization may be performed in a mixed solution of methanol and ethanol. The process of crystallization itself may be performed in accordance with any one of generally employed crystallization methods. The present invention will be explained in detail taking the methanol crystallization and more specifically methanol crystallization of 5'-GMP2Na as an example. First, a methanol solution having a predetermined concentration is placed in a container, such as a can for crystallization, and then, kept at a predetermined temperature. To the container, an aqueous solution containing 5'-GMP2Na and an aqueous solution containing methanol in a high concentration are added. After completion of the addition, the solution in the container is cooled to precipitate 5'-GMP2Na crystals in the solution.

The crystals obtained in the crystallization step are recovered from the solution in the solid/liquid separation step. The method of solid/liquid separation is not particularly limited as long as crystals can be separated and recovered from the methanol solution. Therefore, the solid/liquid separation can be performed by using any one of the generally accepted methods, for example, filtration.

The crystals separated and recovered in the aforementioned step are subsequently subjected to an overdrying treatment. The "overdrying" as used herein refers to drying excessively. The term "drying excessively" means drying crystals so as to have a reduced water content lower than that of a final crystal product to be obtained. The target water content achieved by the overdrying treatment is preferably 90% or less, and more preferably, 70% or less of the total water content of the final crystal product. More specifically, a product of purine nucleotide derivative disodium crystals, such as 5'-GMP2Na crystals, is generally prepared as dry crystalline powder and adjusted so as to have a hydrate equivalent moisture content of about 7 hydrates to about 7.5 hydrates. The term "a hydrate equivalent moisture content" as used herein means a total amount of water bound to the compound that constitutes the crystals (that is, hydrate) and the amount of water attached to the exterior or surface of the crystals expressed in terms of number of hydrates. Therefore, in the overdrying treatment, the crystals are treated so as to contain water in a hydrate equivalent moisture content of preferably at most 6 hydrates, more preferably 3 to 5 hydrates, and most preferably 3 to 4 hydrates. When expressed in terms of percent by weight, these hydrate equivalent moisture contents corresponds to preferably about 21 wt % or less, more preferably about 15 to 18 wt %, and the most preferably, about 12 to 15 wt %, respectively. The overdrying treatment, together with the humidity control step performed later, makes it possible to reduce the amount of methanol contained by the crystals to a predetermined lower level in a short time.

Drying means to be used for overdrying is not particularly limited as long as it can perform overdrying crystals in the above mentioned manner. For example, a rapid powder dryer is preferably used. When a rapid powder dryer is used, it is preferable that crystals be exposed to hot air at about 100° C. to set the temperature of the crystals, namely, the product temperature, at about 70° C.

The overdried crystals are subjected to a humidity control treatment accompanied by the removal of methanol. The term "humidity control" as used herein refers to controlling the water content of crystals (or crystal powder if the product is in the form of powder) at a desired water content. In the humidity control step of the present invention, methanol is further removed from crystals by bringing the crystals into contact with an aqueous solution containing a hydrophilic organic solvent and then placing the crystals under predetermined conditions including humidity and temperature conditions to control the humidity. Hereinafter, the aqueous solution to be added to crystals in the humidity control step will be referred to as "liquid agent". More specifically, in removing methanol that remains in crystals, the crystals are contacted to an aqueous solution containing a predetermined concentration of hydrophilic organic solvent directly by spraying it to the crystals, mixed while stirring for a while until the water is uniformly mixed with the crystals, and then exposed to air having an appropriate humidity and temperature. In this manner, the attached solvent that has been brought as contained in the liquid agent can be removed and simultaneously methanol present in the crystals can be removed. In the overdrying step, the crystals are once excessively dried and then liquid agent is added to the crystals in the humidity control step. Therefore, in the humidity control step, if an excessive amount of the liquid agent is added to the crystals, the moisture content of the crystals is controlled substantially by a drying treatment.

As the liquid agent, an aqueous solution of a hydrophilic organic solvent is used. By use of an aqueous solution of a hydrophilic organic solvent as the liquid agent, the occurrence of agglomeration of crystals can be suppressed in the humidity control step. Specific examples of the hydrophilic organic solvent include methanol, ethanol, and propanol. Of these, methanol is particularly and preferably used. The hydrophilic organic solvents may be used singly or in combination of two or more of them. The concentration of the solvent contained in the liquid agent used the present invention is not particularly limited; however, 20 to 80 vol % is preferable and 30 to 60 vol % is particularly preferable. If the concentration of the solvent is controlled within the range mentioned above, the agglomeration of crystals can be preferably reduced. The water added may contain a nucleic acid component such as purine nucleotide derivative disodium crystals. Furthermore, the liquid agent may contain an inorganic sodium salt, and an organic acid.

The pH value of the liquid agent is not particularly limited as long as purine nucleotide derivative disodium crystals to be treated can maintain the crystal form. More specifically, the pH of the liquid agent is preferably within the range in which 5'-GMP2Na crystals, 5'-IMP2Na crystals, and I+G mixed crystals, can maintain their crystal forms, that is, within the range of pH 6 to 10, more preferably pH 7 to 8.

The amount of liquid agent is not particularly limited as long as the crystals subjected to the humidity control treatment are sufficiently brought into contact with the liquid agent. The amount of the liquid agent is desirably adjusted to preferably 10% to 50 wt %, and more preferably 20% to 30 wt % of the total water content including the water content of the crystals to be treated. If the amount of liquid agent is set within the aforementioned range, methanol can be sufficiently removed and agglomeration of crystals can be sufficiently suppressed.

In the humidity control step, crystals are placed in a predetermined humidity condition. Therefore, the humidity control step is desirably performed in a humidity-controllable room the humidity condition of the humidity control step, that is, relative humidity, is preferably set within the range of 50% to 90%, and more preferably 60% to 80%. Furthermore, in the humidity control step, it is desirable that not only the humidity condition but also the temperature condition is controlled. The temperature, at which the liquid agent is exposed to and mixed with crystals, is preferably within the range of 10° C. to 50° C., and more preferably 35° C. to 45° C. After the liquid agent and the crystals are mixed with each other, the temperature of the mixture is preferably set at atmospheric temperature (room temperature), preferably 20° C. to 50° C. and more preferably 35° C. to 45° C. Under these humidity and temperature conditions, methanol can be efficiently removed while suppressing crystal agglomeration up to a degree that causes substantially no problem.

The humidity control is preferably performed by placing crystals in a humidity controlled chamber while supplying air to the chamber. Removal of a solvent from the liquid agent and methanol from the crystals can be performed simply by exposing the crystals in a still state to air; however, this purpose can be attained more quickly by moving the crystals by the supplied air flow.

Although the present invention has been explained above referring to the embodiment that includes crystallization of purine derivative nucleotide disodium in methanol, in another embodiment, the present invention is not limited thereto but is also applicable to production of purine derivative nucleotide disodium crystals whose methanol content has been decreased to a predetermined acceptable level starting from purine derivative nucleotide disodium crystals containing methanol in unacceptable amounts or dispersions containing such crystals.

Although the present invention has been explained above referring to removal of methanol, the present invention is not limited thereto but is also applicable to removal of ethanol or a mixture of methanol and ethanol and production of crystals involving removal of ethanol or a mixture of methanol and ethanol. One skilled in the art will readily understand that similar effects can be obtained when ethanol or a mixture of methanol and ethanol is used.

Also, the present invention provides a method of removing an alcohol such as methanol, ethanol or a mixture thereof from purine nucleotide derivative disodium crystals containing methanol. The method of removing an alcohol such as methanol, ethanol or a mixture thereof from crystals according to the present invention includes at least the overdrying step and humidity control step in the production method according to the present invention mentioned above. Preferable conditions of each step are the same as those mentioned above. According to the method of removing an alcohol such as methanol, ethanol or a mixture thereof according to the present invention, the alcohol such as methanol, ethanol or a mixture thereof can be efficiently removed from purine nucleotide derivative disodium crystals containing methanol while suppressing agglomeration of crystals.

EXAMPLES

The present invention will be described in more detail by way of examples, which should not be construed as limiting the scope of the present invention.

Example 1

First, 320 milliliters (ml) of an aqueous solution of 55 vol % methanol was placed in a separable crystallization can and maintained at 40° C. Then, 781.0 grams (g) of an aqueous solution of 187.4 g of 5'-GMP2Na and an aqueous solution of 95 vol % methanol were simultaneously added to the can to bring the final methanol concentration in the crystallization can to 55 vol %. After completion of the addition, the resultant solution was cooled to 10° C. to precipitate 5'-GMP2Na crystals.

Then, solid-liquid separation was performed to obtain 5'-GMP2Na crystals, which were subsequently subjected to an overdrying treatment using a rapid powder dryer (TG100, manufactured by Retch Co., Ltd.) while supplying hot air at 100° C. to set the crystal temperature at 70° C. The obtained crystals contained 18 wt % of water and 6,500 parts per million (ppm) of methanol.

After the overdrying treatment, 11 g of an aqueous solution of 30 vol % methanol was added to 150 g of the crystals by means of an atomizer. The resultant mixture was mixed with stirring and dried at 35° C. and a relative humidity of 80% for 2 hours. The remaining methanol concentration of the obtained crystals was 9 ppm as determined by gas chromatography and the percentage of crystal agglomeration was 0.2 wt %.

Example 2

First, 300 ml of an aqueous solution of 55 vol % methanol was placed in a separable crystallization can and maintained at 40° C. Then, 663.0 g of an aqueous solution of 159.1 g of 5'-GMP2Na and an aqueous solution of 95 vol % methanol were simultaneously added to the can to bring the final concentration of methanol in the crystallization can to 55 vol %. After completion of the addition, the resultant solution was cooled to 10° C. to precipitate 5'-GMP2Na crystals.

Then, solid-liquid separation was performed to obtain 5'-GMP2Na crystals, which were subsequently subjected to an overdrying treatment using a rapid powder dryer while supplying hot air at 100° C. to set a crystal temperature at 70° C. The obtained crystals contained 17 wt % of water and 8,100 ppm of methanol.

After the overdrying treatment, 10 g of an aqueous solution of 40 vol % ethanol was added to 100 g of the crystals by means of an atomizer. The resultant mixture was mixed with stirring and dried at 40° C. and a relative humidity of 90% for 3 hours. The remaining methanol concentration of the obtained crystals was 20 ppm and the percentage of crystal agglomeration was 0.3 wt %.

Example 3

First, 280 ml of an aqueous solution of 55 vol % methanol was placed in a separable crystallization can and maintained at 40° C. Then, 663.0 g of an aqueous solution of 159.1 g of 5'-GMP2Na and an aqueous solution of 95 vol % methanol were simultaneously added to the crystallization can to bring the final concentration of methanol in the crystallization can to 55 vol %. After completion of the addition, the resultant solution was cooled to 10° C. to precipitate 5'-GMP2Na crystals.

Then, solid-liquid separation was performed to obtain crystals, which were subsequently subjected to an overdrying treatment using a rapid powder dryer while supplying hot air at 100° C. to set the crystal temperature at 70° C. The obtained crystals contained 17 wt % of water and 7,500 ppm of methanol. After the overdrying treatment, 10.9 g of an aqueous solution containing 30 vol % propanol was added to 100 g of the crystals by means of an atomizer. The resultant mixture was mixed with stirring, and dried at 40° C. and a relative humidity of 90% for 2 hours. The remaining methanol content of the crystals was 28 ppm and the percentage of obtained crystal agglomeration was 1.1 wt %.

Example 4

First, 600 ml of an aqueous solution of 45 vol % methanol was placed in a metal vat and maintained at 45° C. Then, 3,448.8 g of aqueous solution containing 358.0 g of 5'-IMP2Na and 364.4 g of 5'-GMP2Na and an aqueous solution of 95 vol % methanol were simultaneously added to the vat to bring the final concentration of methanol in the crystallization can to 45 vol %. After completion of the addition, the resultant solution was cooled to 10° C. to precipitate 5'-IMP2Na and 5'-GMP2Na mixed crystals.

Then, solid-liquid separation was performed to obtain the mixed crystals, which were subsequently subjected to an overdrying treatment using a rapid powder dryer while supplying hot air at 100° C. to set the crystal temperature at 70° C. The obtained I+G crystals contained 19 wt % of water and 3,100 ppm of methanol.

After the overdrying treatment, 41 g of an aqueous solution of 20 vol % methanol was added to 550 g of the crystals by means of an atomizer. The resultant mixture was mixed with stirring, and dried at 30° C. and a relative humidity of 70% for 3 hours. The remaining methanol concentration of the crystals was 26 ppm and the percentage of crystal agglomeration was 0.5 wt %.

Example 5

First, 600 ml of an aqueous solution containing 55 vol % methanol was placed in a metal vat and maintained at 45° C. Then, to 3,448.80 g of an aqueous solution of 358.0 g of 5'-IMP2Na, an aqueous solution of 98 vol % methanol was added to bring the final concentration of methanol to 55 vol % while keeping the temperature of 45° C. during the addition. After completion of the addition, the resultant solution was cooled to 10° C. to precipitate 5'-IMP2Na crystals.

Then, solid-liquid separation was performed to obtain 5'-IMP2Na crystals, which were subsequently subjected to an overdrying treatment using a rapid powder dryer while supplying hot air at 100° C. to set the crystal temperature at 70° C.

After the overdrying treatment, the obtained crystals contained 21 wt % of water and 2,100 ppm of methanol. Subsequently, 10.87 g of an aqueous solution of 30 vol % of methanol was added to 200 g of the crystals by means of an atomizer. The resultant mixture was mixed with stirring and dried at 30° C. and a relative humidity of 70% for 3 hours. The remaining methanol concentration of the crystals was 7 ppm and the percentage of crystal agglomeration was 0.7 wt %.

Comparative Example 1

First, 300 milliliters of an aqueous solution of 55 vol % methanol was placed in a separable crystallization can and maintained at 40° C. Then, 664.0 g of an aqueous solution containing 158.1 g of 5'-GMP2Na and an aqueous solution containing 95 vol % methanol were simultaneously added to the can to bring the final concentration of methanol in the crystallization can to 55 vol %. After completion of the addition, the resultant mixture was cooled to 10° C. to precipitate 5'-GMP2Na crystals.

Then, solid-liquid separation was performed to obtain 5'-GMP2Na crystals, which were subsequently subjected to an overdrying treatment using a rapid powder dryer while supplying hot air at 10° C. to set the crystal temperature at 70° C.

After the overdrying treatment, the obtained crystals contained 20 wt % of water and 9,500 ppm of methanol. Subsequently, 40 g of the crystals was allowed to stand at 27° C. and a relative humidity of 57% to dry. The remaining methanol concentration of the crystals obtained after 24 hours was 998 ppm and the percentage of crystal agglomeration in terms of a rate of amount of crystals that did not pass through a sieve having a mesh size of 500 micrometers, was 3 wt %.

Comparative Example 2

First, 300 ml of an aqueous solution of 55 vol % methanol was placed in a separable crystallization can and maintained at 40° C. Then, 662.1 g of an aqueous solution of 159.7 g of 5'-GMP2Na and an aqueous solution of 95 vol % methanol were simultaneously added to the can to bring the final concentration of methanol in the crystallization can to 55 vol %. After completion of the addition, the resultant mixture was cooled to 10° C. to precipitate 5'-GMP2Na crystals.

Then, solid-liquid separation was performed to obtain 5'-GMP2Na crystals, which were subjected to an overdrying treatment using a rapid powder dryer while supplying hot air at 100° C. to set the crystal temperature at 70° C. The obtained crystals contained 17 wt % of water and 7,100 ppm of methanol.

After the overdrying treatment, 51 g of the obtained crystals was allowed to stand at 35° C. and a relative humidity of 80% to dry. The concentration of the remaining methanol was 150 ppm and the percentage of crystal agglomeration was 5 wt %.

Comparative Example 3

First, 550 ml of an aqueous solution of 45 vol % methanol was placed in a separable crystallization can and maintained at 45° C. Then, 3,161.4 g of an aqueous solution of 392.36 g of 5'-IMP2Na, 335.2 g of 5'-GMP2Na, and an aqueous solution of 95 vol % methanol were simultaneously added to the can to bring the final concentration of methanol in the crystallization can to 45 vol %. After completion of the addition, the resultant mixture was cooled to 10° C. to precipitate I+G mixed crystals.

Then, solid-liquid separation was performed to obtain I+G mixed crystals, which were subsequently subjected to an overdrying treatment while supplying hot air at 100° C. to set the crystal temperature at 70° C. The obtained aqueous solution contained 22 wt % of water and 2,130 ppm of methanol.

After the overdrying treatment, 45 g of pure water was added to 450 g of mixed crystals by means of an atomizer. The resultant mixture was mixed with stirring and dried at 25° C. and a relative humidity of 70% for 6 hours. The remaining methanol concentration of the crystals was 38 ppm, the water content was 23 wt %, and the percentage of crystal agglomeration was 4.5 wt %.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A method of producing purine nucleotide disodium crystals, comprising:
   crystallizing a purine nucleotide disodium in a solution of alcohol comprising one member selected from the group consisting of methanol, ethanol, and mixtures of methanol and ethanol, to obtain purine nucleotide disodium crystals which contain an alcohol;
   performing solid-liquid separation of said purine nucleotide disodium crystals which contain an alcohol, to obtain separated purine nucleotide disodium crystals;

overdrying said separated purine nucleotide disodium crystals, to obtain overdried purine nucleotide disodium crystals; and bringing said overdried purine nucleotide disodium crystals into contact with an aqueous solution which comprises a hydrophilic organic solvent, to control the humidity of the purine nucleotide disodium crystals under a predetermined humidity condition, wherein said hydrophilic organic solvent is at least one alcohol selected from the group consisting of methanol, ethanol, propanol, and mixtures thereof, to obtain purine nucleotide disodium crystals which have an alcohol content which is lower than said purine nucleotide disodium crystals which contain an alcohol.

2. The method according to claim 1, wherein said overdrying comprises drying said separated purine nucleotide disodium crystals with the controlled humidity to a hydrate equivalent water content of at most 5 hydrates.

3. The method according to claim 1, wherein said predetermined humidity condition is a relative humidity of 20% to 90%.

4. The method according to claim 2, wherein said predetermined humidity condition is a relative humidity of 20% to 90%.

5. The method according to claim 1, wherein said purine nucleotide disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

6. The method according to claim 2, wherein said purine nucleotide disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

7. A method of removing an alcohol from purine nucleotide disodium crystals, comprising:

overdrying purine nucleotide disodium crystals which contain an alcohol comprising one member selected from the group consisting of methanol, ethanol, and mixtures of methanol and ethanol, to obtain overdried purine nucleotide disodium crystals; and bringing said overdried purine nucleotide disodium crystals into contact with an aqueous solution comprising a hydrophilic organic solvent, to control the humidity of said purine nucleotide disodium crystals under a predetermined humidity condition, wherein said hydrophilic organic solvent is at least one alcohol selected from the group consisting of methanol, ethanol, propanol, and mixtures thereof, to obtain purine nucleotide disodium crystals which have an alcohol content which is lower than said purine nucleotide disodium crystals which contain an alcohol.

8. The method according to claim 7, wherein said purine nucleotide disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

9. A method of producing purine nucleotide disodium crystals, comprising:

performing solid-liquid separation of purine nucleotide disodium crystals which contain an alcohol comprising one member selected from the group consisting of methanol, ethanol, and mixtures of methanol and ethanol, to obtain separated purine nucleotide disodium crystals;

overdrying said separated purine nucleotide disodium crystals, to obtain overdried purine nucleotide disodium crystals; and bringing said overdried purine nucleotide disodium crystals into contact with an aqueous solution comprising a hydrophilic organic solvent, to control the humidity of the purine nucleotide disodium crystals under a predetermined humidity condition;

wherein said hydrophilic organic solvent is at least one alcohol selected from the group consisting of methanol, ethanol, propanol, and mixtures thereof, to obtain purine nucleotide disodium crystals which have an alcohol content which is lower than said purine nucleotide disodium crystals which contain an alcohol.

10. The method according to claim 9, wherein said overdrying comprises drying said purine nucleotide disodium crystals with the controlled humidity to a hydrate equivalent water content of at most 5 hydrates.

11. The method according to claim 9, wherein said predetermined humidity condition is a relative humidity of 20% to 90%.

12. The method according to claim 9, wherein said purine nucleotide disodium crystals comprise at least one member selected from the group consisting of 5'-guanylic acid disodium crystals, 5'-inosinic acid disodium crystals, and mixed crystals of 5'-guanylic acid disodium and 5'-inosinic acid disodium.

13. The method according to claim 7, wherein said overdrying comprises drying said purine nucleotide disodium crystals with the controlled humidity to a hydrate equivalent water content of at most 5 hydrates.

14. The method according to claim 7, wherein said predetermined humidity condition is a relative humidity of 20% to 90%.

15. The method according to claim 1, wherein said bringing said overdried purine nucleotide disodium crystals into contact with an aqueous solution which comprises a hydrophilic organic solvent comprises spraying said aqueous solution on said overdried purine nucleotide disodium crystals.

16. The method according to claim 7, wherein said bringing said overdried purine nucleotide disodium crystals into contact with an aqueous solution which comprises a hydrophilic organic solvent comprises spraying said aqueous solution on said overdried purine nucleotide disodium crystals.

17. The method according to claim 9, wherein said bringing said overdried purine nucleotide disodium crystals into contact with an aqueous solution which comprises a hydrophilic organic solvent comprises spraying said aqueous solution on said overdried purine nucleotide disodium crystals.

* * * * *